United States Patent
Cade et al.

(10) Patent No.: US 6,517,865 B2
(45) Date of Patent: Feb. 11, 2003

(54) POLYMER FILM COMPOSITIONS FOR CAPSULES

(75) Inventors: Dominique Cade, Colmar (FR); Robert Scott, Sint-Niklaas (BE); Xiongwei He, Colmar (FR)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 10/157,428

(22) Filed: May 28, 2002

(65) Prior Publication Data

US 2002/0187190 A1 Dec. 12, 2002

Related U.S. Application Data

(63) Continuation of application No. 08/859,310, filed on May 20, 1997, now abandoned.

(30) Foreign Application Priority Data

Dec. 17, 1996 (FR) .............................. 96 15580

(51) Int. Cl.[7] .............................. A61K 9/48; A61K 9/20; A61K 9/28; A61K 9/36
(52) U.S. Cl. ..................... 424/451; 424/454; 424/464; 424/474; 424/480; 424/482
(58) Field of Search ................. 424/451, 454, 424/464, 474, 480, 482

(56) References Cited

U.S. PATENT DOCUMENTS 5,431,917 A * 7/1995 Yamamoto et al.

* cited by examiner

*Primary Examiner*—Thurman K. Page
*Assistant Examiner*—Humera N. Sheikh
(74) *Attorney, Agent, or Firm*—Evan J. Federman

(57) ABSTRACT

The present invention relates to non-animal polymer compositions suitable for film forming, particularly hard and soft capsules, comprising water soluble cellulose ethers, hydrocolloides and sequestering agents.

21 Claims, No Drawings

POLYMER FILM COMPOSITIONS FOR CAPSULES

This application is a continuation of 08/859,310 filed May 20, 1997 now abandoned.

BACKGROUND OF THE INVENTION

1. Field of the Invention

The present invention relates to non-animal polymer compositions suitable for film forming, particularly hard and soft capsules, comprising water soluble cellulose ethers, hydrocolloids and sequestering agents.

2. Description of Related Art

Capsules are widely used in the pharmaceutical industry as well as in the health food supplement market. The main usage thereof is as dosage form for solid, semi-solid, liquid, pellet or herbal preparations. A primary objection of these dosage forms is to have a good disintegration after being administered in order to enable an effective dissolution of the active substances in the appropriate digestive organ. Consequently, this disintegration characteristic has to remain stable over time when finished products are stored prior to use.

The traditional material for forming the capsule shell is gelatin, because it has the correct and quite ideal properties. Nevertheless, gelatin has some disadvantages which make it necessary to have other capsule shell materials available. A major unfavorable aspect is the animal origin of gelatin. Other disadvantages are the inconveniences of relatively high water content (10–17%) and the loss of elasticity with decreasing water content. Furthermore gelatin capsules are sensitive to heat and humidity which affects the usability of the product. In particular, soft gelatin capsules are known to aggregate under hot and humid conditions. Under dry conditions gelatin films may induce static charge build up affecting later processing.

As a gelatin substitute the use of water soluble film forming cellulose derivatives is widely described in the literature. Reports of capsules made from cellulose derivatives refer to poor disintegration in vivo especially when compared with gelatin. To overcome this drawback in EP0714656 it is suggested to use hydroxypropylmethylcellulose (HPMC) with a viscosity of 2.4 to 5.4 centistokes in 2% aqueous solution at 20° C. with carrageenan as gelling agent and calcium or potassium ions as co-gelling agent. However the very low viscosity of HPMC resulting from lower molecular weight chains induces higher film brittleness. Furthermore, the use of this composition results in an undesirable loss of transparency of the film. Attempts to improve transparency are disclosed in EP0592130 by exposing BPMC to UV radiation prior to capsule processing.

SUMMARY OF THE INVENTION

It has been found that a polymer film composition for capsules wherein the ratios of cellulose ethers, hydrocofloids and sequestering agents are 90 to 99.98% by weight of a cellulose ether or mixture of cellulose ethers with a water content of 2 to 10%, 0.01 to 5% by weight of a hydrocolloid or mixtures of hydrocofloids, and 0.01 to 5% by weight of a sequestering agent or agents do not have the mentioned disadvantages.

DETAILED DESCRIPTION OF THE PREFERRED EMBODIMENTS

Suitable cellulose ethers for the present invention are alkyl and/or hydroxyalkyl substituted cellulose ether with 1 to 4 carbon atoms in the alkyl chains, preferably methyl cellulose, hydroxyethyl cellulose, hydroxypropyl cellulose, hydroxyethylmethyl cellulose, hydroxyethylethyl cellulose, hydroxypropylmethyl cellulose or the like. Especially preferred is HBPMC. The amount of the cellulose ether or mixture of cellulose ethers is preferably 95 to 99.98% by weight. The viscosity of the cellulose ether or blend is 3 to 15 cps in 2% aqueous solution at 20° C., preferred 5 to 10, especially preferred 6 cps.

Suitable hydrocolloids include such items as synthetic gums which are capable of gelling without the addition of alkaline or alkaline earth metal ions. The preferred gum for this purpose is gellan gum. Such gum, particularly including gellan gum, may be combined in mixtures producing synergistic properties which mixtures may also include natural seaweeds, natural seed gums, natural plant exudates, natural fruit extracts, bio-synthetic gums, bio-synthetic processed starch or cellulosic materials. More specifically, the mixture may include alginates, agar gum, guar gum, locust bean gum (carob), carrageenan, tara gum, gum arabic, ghatti gum, Khaya grandifolia gum, tragacanth gum, karaya gum, pectin, arabian (araban), xanthan, gellan, starch, Konjac mannan, galactomannan, funoran, and other exocellular polysaccharides of which are preferred the exocellular polysaccharides, such as xanthan, acetan, gellan, welan, rhamsan, furcelleran, succinoglycan, scieroglycan, schizophyflan, tamarind gum, curdlan, pullulan, dextran. The amount of gum present is preferably 0.01 to 2% by weight and especially preferred 0.1 to 1.0%.

The preferred sequestering agents are ethylenediaminetetraacetic acid, acetic acid, boric acid, citric acid, gluconic acid, lactic acid, phosphoric acid, tartaric acid or salts thereof methaphosphates, dihydroxyethylglycine, lecithin or beta cyclodextrin and combinations thereof Especially preferred is ethylenediaminetetraacetic acid or salts thereof or citric acid or salts thereof The amount is preferably 0.01 to 3%, especially 0.1 to 2% by weight.

The sequestering mechanism can be adjusted by addition of either monovalent or divalent cations, such a $Ca^{++}$, $Mg^{++}$, $K^+$, $Na^+$, $Li^+$, $NH_4^+$ or the like.

Capsules or films with the inventive polymer composition may be manufactured with conventional machines by the conventional processes like extrusion moulding, injection moulding, casting or dip moulding.

The capsules and films have a non-animal polymer composition, an improved dissolution behavior, an enhanced elasticity and show higher transparency. The enhanced elasticity makes the capsules more useful for inhalation products. Furthermore the capsules are not sensitive to formaldehyde, for e.g. from a contaminated fill and they have a better temperature stability compared to gelatin capsules, because a crosslinking at storage on elevated temperatures does not occur.

The inventive polymer composition may contain additionally acceptable plasticizers in a range from about 0 to 40% based upon the weight of the cellulose ether. Suitable plasticizers are polyethylene glycol, glycerol, sorbitol, sucrose, corn syrup, fructose, dioctyl-sodium sulfosuccinate, triethyl citrate, tributyl citrate, 1,2-propylenglycol, mono-, di- or triacetates of glycerol, natural gums or the like as well as mixtures thereof.

The inventive polymer composition may contain in a further aspect additionally pharmaceutically or food acceptable coloring agents in the range of from about 0 to about 10% based upon the weight of the cellulose ether. The coloring agents may be selected from azo-, quinophthalone-, triphenylmethane-, xanthene- or indigoid dyes, iron oxides or hydroxides, titanium dioxide or natural dyes or mixtures thereof. Examples are patent blue V, acid brilliant green BS, red 2G, azorubine, ponceau 4R, amaranth, D+C red 33, D+C red 22, D+C red 26, D+C red 28, D+C yellow 10-, yellow 2G, FD+C yellow 5, FD+C yellow 6, FD+C red 3, D+C red 40, FD+C blue 1, FD+C blue 2, FD+C green 3, brilliant black BN, carbon black, iron oxide black, iron oxide red, iron oxide yellow, titanium dioxide, riboflavin, carotenes, anthocyanines, turmeric, cochineal extract, clorophyllin, canthaxanthin, caramel, or betanin.

The shaped polymer composition of the invention or the final product thereof may be coated with a suitable coating agent like cellulose acetate phthalate, polyvinyl acetate phthalate, methacrylic acid polymers, hypromellose phthalate, hydroxypropylmethyl cellulose phthalate, hydroxyalkyl methyl cellulose phthalates or mixtures thereof to provide e.g. enteric properties.

The polymer composition of the invention may be used for the production of containers for providing unit dosage forms for example for agrochemicals, seeds, herbs, foodstuffs, dyestuffs, pharmaceuticals, flavoring agents and the like.

The improved elasticity of the inventive polymer composition makes it useful for the encapsulation of caplets in a capsule, especially in a tamper-proof form. The encapsulation of a caplet in a capsule is preferred processed by cold shrinking together capsule parts, which are filled with a caplet, which comprises the steps providing empty capsule parts, filling at least one of said capsule parts with one or more caplets, putting said capsule parts together, and treating the combined capsule parts by cold shrinking.

The inventive polymer composition is also useful for encapsulating and sealing the two capsule halves in a process in which one or more layers of the composition are applied over the seam of the cap and body, or by a liquid fusion process wherein the filled capsules are wetted with a hydroalcoholic solution that penetrates into the space where the cap overlaps the body, and then dried.

The improved properties of the polymer composition are demonstrated by the following composition and comparative examples.

COMPOSITION EXAMPLES:

| COMPONENTS | COMPOS 1 | COMPOS. 2 | COMPOS. 3 | COMPOS. 4* |
|---|---|---|---|---|
| HPMC(1) | 99.26% | 99.62% | 99.46% | 98.1% |
| Gellan | 0.54% | 0.22% | 0.54% | 0 |
| Na citrate | 0.20% | 0 | 0 | 0 |
| Citric Acid | 0 | 0.16% | 0 | 0 |
| Carrageenan | 0 | 0 | 0 | 1.3% |
| KCl | 0 | 0 | 0 | 0.6% |

*According to EP0714656
(1)HPMC equilibrated at 50% RH (equivalent to a water content between 5 to 7%)

Composition 5: Conventional transparent hard gelatin capsule
Composition 6: Conventional opaque hard gelatin capsule Mechanical impact test:
Capsule body parts are submitted to mechanical impact stress of 80 mJ and the percentage of fractured capsules are checked.

| EQUILIBRIUM RH | COMPOS. 1 | COMPOS. 2 | COMPOS. 5 | COMPOS. 6 |
|---|---|---|---|---|
| 50% | 0 | 0 | 0 | 0 |
| 10% | 0 | 0 | 0 | 5 |
| 2.5% | 0 | 0 | 10 | 45 |

Inhalator piercing test:
Capsules are pierced by inhalator device and the percentage of cracks and/or fracture is recorded.

| EQUILIBRIUM RH | COMPOS. 1 | COMPOS. 2 | COMPOS. 5 | COMPOS. 6 |
|---|---|---|---|---|
| 50% | 0 | 0 | 0 | 0 |
| 10% | 0 | 0 | 95 | 80 |
| 2.5% | 0 | 0 | 95 | 75 |

Capsule transparency test:
Capsule bodies are measured for transmittance at 650 nm

| CAPSULE | TRANSPARENCY |
|---|---|
| Composition 1 | 74% |
| Composition 2 | 75% |
| Composition 4 | 60% |
| Composition 5 | 81% |

Dissolution test:
Acetaminophen dissolved from capsules immersed in deionised water at 37° C. (USP XXII), listed is the percentage of acetaminophen after 45 min.

| CAPSULE | % DISSOLVED |
|---|---|
| Composition 1 | 90% |
| Composition 2 | 90% |
| Composition 3 | 63% |
| Composition 5 | 91% |

Dissolution test after exposure to crosslinking agent:
Capsules were filled with lactose containing 40 ppm of HCHO and stored under room conditions for one month, measured is the percentage of acetaminophen dissolved after 45 min.

| CAPSULE | % DISSOLVED |
|---|---|
| Composition 1 | 90% |
| Composition 5 | 22% |

Moisture exchange test:
Capsules were filled with dry carboxymethylcellulose sodium salt (CMC) and stored in closed bottle under room conditions.

| CAPSULE | INITIAL WATER CONTENT | | FINAL WATER CONTENT | |
|---|---|---|---|---|
| | Capsule | Fill | Capsule | Fill |
| Composition 1 | 6.4% | 0% | 1.4% | 1.1% |
| Composition 5 | 14% | 0% | 4.7% | 2.0% |

What is claimed is:

1. A capsule material based on a polymer composition comprising:
    a) 90 to 99.98% by weight of at least one cellulose ether having a water content of 2 to 10% and a viscosity of 3 to 15 cps measured in a 2% aqueous solution at 20° C.;
    b) 0.01 to 5% by weight of gellan gum; and
    c) 0.01 to 8% by weight of a sequestering agent selected from the group consisting of ethylenediaminetetraacetic acid, sodium citrate, citric acid and combinations thereof.

2. A capsule material according to claim 1, wherein the at least one cellulose ether is selected from the group consisting of alkyl substituted cellulose ethers, hydroxyalkyl substituted cellulose ethers, and combinations thereof, wherein the alkyl group has 1 to 4 carbon atoms.

3. A capsule material according to claim 1, wherein the at least one cellulose ether is selected from the group consisting of methyl cellulose, hydroxyethyl cellulose, hydroxypropyl cellulose hydroxyethylmethyl cellulose, hydroxyethylethyl cellulose, hydroxypropylmethyl cellulose (HPMC) and combinations thereof.

4. A capsule material according to claim 1, wherein the cellulose ether is hydroxypropylmethyl cellulose (HPMC).

5. A capsule material according to claim 1, wherein the sequestering agent is ethylenediaminetetraacetic acid.

6. A capsule material according to claim 1, wherein
    a) the at least one cellulose ether is present in an amount of 95 to 99.98% by weight;
    b) the gellan gum is present in an amount of 0.01 to 2% by weight; and
    c) the sequestering agent is present in an amount of 0.01 to 3% by weight.

7. A capsule material according to claim 1, wherein the at least one cellulose ether has a viscosity of 5 to 10 measured in a 2% aqueous solution at 20° C.

8. A capsule material according to claim 7 wherein the at least one cellulose ether has a viscosity of 6 cps measured in a 2% aqueous solution at 20° C.

9. A capsule material according to claim 1, further comprising at least one plasticizer in an amount of up to 40% by weight based on the weight of the at least one cellulose ether.

10. A capsule material according to claim 9 wherein the plasticizer is selected from the group consisting of polyethylene glycol, glycerol, sorbitol, sucrose, corn syrup, fructose, dioctysodium sulfosuccinate, treithyl citrate, tributyl citrate, 1,2-propyleneglycol, mono-, di- or triacetates of glycerol, natural gums, and combinations thereof.

11. A capsule material according to claim 1, further comprising at least one coloring agent in an amount of up to 10% by weight, based on the weight of the at least one cellulose ether.

12. A capsule material according to claim 11 wherein the coloring agent is selected from the group consisting of azo-, quinophthalone-, triphenylmethane-, xanthene- and indigo dyes, iron oxides, iron hydroxides, titanium dioxide, natural dyes, and combinations thereof.

13. A capsule material according to claim 11 wherein the coloring agent is selected from the group consisting of patent blue V, acid brilliant green BS, red 2G, azorubine, ponceau 4R, amaranth, D+C red 33, D+C red 22, D+C red 26, D+C red 28, D+C yellow 10, yellow 2 G, FD+C yellow 5, FD+C yellow 6, FD+C red 3, FD+C red 40, FD+C blue 1, FD+C blue 2, FD+C green 3, brilliant black BN, and combinations thereof.

14. A capsule material according to claim 11 wherein the coloring agent is selected from the group consisting of carbon black, iron oxide black, iron oxide red, iron oxide yellow, titanium dioxide, riboflavin, carotenes, anthocyanines, turmeric, cochineal extract, clorophyllin, canthaxanthin, caramel, betanin and combinations thereof.

15. A container for housing a unit dosage form of an agrochemical, seed, herb, foodstuff, dyestuff, pharmaceutical, or flavoring agent produced from a capsule material based on a polymer composition comprising:
    a) 90 to 99.98% by weight of at least one cellulose ether having a water content of 2 to 10% and a viscosity of 3 to 15 cps measured in a 2% aqueous solution at 20° C.;
    b) 0.01 to 5% by weight of gellan gum; and
    c) 0.01 to 8% by weight of a sequestering agent selected from the group consisting of ethylenediaminetetraacetic acid, sodium citrate, citric acid and combinations thereof.

16. A container of claim 15, in the form of a capsule for housing a pharmaceutically active agent.

17. A container according to claim 14 wherein the capsule comprises a coating.

18. A container according to claim 17, wherein the coating is made from a material selected from the group consisting of cellulose acetate phthalate, polyvinyl acetate phthalate, methacrylic acid polymers, hydromellose phthalate, hydroxypropylmethyl cellulose phthalate, hydroxyalkylmethyl cellulose phthalate, and combinations thereof.

19. A container according to claim 15, wherein the container is a capsule containing two capsule halves and the capsule halves are sealed together with at least one layer of the capsule material.

20. A container according to claim 15, wherein the container is a capsule containing two capsule halves and the capsule halves are sealed by a liquid fusion process.

21. Caplets encapsulated in a capsule material according to claim 1.

* * * * *